United States Patent
Mackenzie et al.

(10) Patent No.: US 6,245,871 B1
(45) Date of Patent: Jun. 12, 2001

(54) GROUP 8-10 TRANSITION METAL OLEFIN POLYMERIZATION CATALYSTS

(75) Inventors: Peter Borden Mackenzie, Kingsport; Christopher Moore Killian, Gray; Leslie Shane Moody, Johnson City, all of TN (US); Jason Patrick McDevitt, Wake Forest, NC (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/226,116

(22) Filed: Jan. 7, 1999

Related U.S. Application Data

(63) Continuation-in-part of application No. 09/028,316, filed on Feb. 24, 1998, now abandoned.
(60) Provisional application No. 60/045,355, filed on May 2, 1997, provisional application No. 60/045,333, filed on May 1, 1997, and provisional application No. 60/044,691, filed on Apr. 18, 1997.

(51) Int. Cl.$^7$ ............................. C08F 4/60; C08F 4/602
(52) U.S. Cl. ................... 526/141; 526/147; 526/161; 526/171; 526/172; 502/117; 502/155; 556/35
(58) Field of Search ................... 526/161, 171, 526/172, 141, 147

(56) References Cited

U.S. PATENT DOCUMENTS

| | | |
|---|---|---|
| 4,482,640 | 11/1984 | Knudsen et al. . |
| 4,659,685 | 4/1987 | Coleman, III et al. . |
| 4,689,437 | 8/1987 | Murray . |
| 4,691,036 | 9/1987 | Starzewski et al. . |
| 4,716,138 | 12/1987 | Murray . |
| 4,716,205 | 12/1987 | Klabunde . |
| 4,724,273 | 2/1988 | Fink et al. . |
| 4,906,754 | 3/1990 | Klabunde . |
| 5,030,606 | 7/1991 | Klabunde . |
| 5,175,326 | 12/1992 | Klabunde . |
| 5,272,124 | 12/1993 | Wu . |
| 5,571,881 | 11/1996 | Goodall et al. . |
| 5,714,556 | 2/1998 | Johnson et al. . |
| 5,852,145 | 12/1998 | McLain et al. . |
| 5,866,663 | 2/1999 | Brookhart et al. . |
| 5,880,241 | 3/1999 | Brookhart et al. . |
| 5,880,323 | 3/1999 | Brookhart, III et al. . |
| 5,886,224 | 3/1999 | Brookhart et al. . |
| 5,891,963 | 4/1999 | Brookhart et al. .......... 525/326.1 |

FOREIGN PATENT DOCUMENTS

| | | |
|---|---|---|
| 292 251 A5 | 7/1991 | (DE) . |
| 0 381 495 | 8/1990 | (EP) . |
| 0 454 231 A2 | 10/1991 | (EP) . |
| 0 531 174 A2 | 3/1993 | (EP) . |
| 9-255712 | 9/1997 | (JP) . |
| 9-272709 | 10/1997 | (JP) . |
| 9-272713 | 10/1997 | (JP) . |
| WO 95/14048 | 5/1995 | (WO) . |
| WO 96/23010 | 8/1996 | (WO) . |
| WO 96/37522 | 11/1996 | (WO) . |
| WO 96/37523 | 11/1996 | (WO) . |
| WO 96/37528 | 11/1996 | (WO) . |
| WO 96/37529 | 11/1996 | (WO) . |
| WO 97/02298 | 1/1997 | (WO) . |
| WO 97/17380 | 5/1997 | (WO) . |
| WO 97/38024 | 10/1997 | (WO) . |
| WO 97/48735 | 12/1997 | (WO) . |
| WO 97/48736 | 12/1997 | (WO) . |
| WO 97/48737 | 12/1997 | (WO) . |
| WO 97/48739 | 12/1997 | (WO) . |
| WO 97/48740 | 12/1997 | (WO) . |
| WO 97/48742 | 12/1997 | (WO) . |
| WO 97/48777 | 12/1997 | (WO) . |
| WO 98/03521 | 1/1998 | (WO) . |
| WO 98/03559 | 1/1998 | (WO) . |
| WO 98/03617 | 1/1998 | (WO) . |
| WO 98/27124 | 6/1998 | (WO) . |
| WO 98/30609 | 7/1998 | (WO) . |

(List continued on next page.)

OTHER PUBLICATIONS

Claudio Pettinari et al., "Tin(IV) and organotin (IV) complexes containing mono or bidentate N–donor ligands; II. 4–Phenylimidazole derivatives. Crystal and molecular structure of bis(4–phenylimidazole) trimethylin(IV) chloride", *Journal of Organometallic Chemistry* 515 (1996) 119–130.

(List continued on next page.)

*Primary Examiner*—David W. Wu
*Assistant Examiner*—R. Rabago
(74) *Attorney, Agent, or Firm*—Harry J. Gwinnell; Jonathon D. Wood

(57) ABSTRACT

Provided are certain transition metal complexes which are useful as catalysts in the polymerization of olefinic monomers. In particular, the invention provides complexes of certain bidentate ligands bonded to Ni, Pd, Co, or Fe, and optionally, one or more neutral Lewis acids, and their use in the polymerization of olefins. Suitable complexes include those of the following structure:

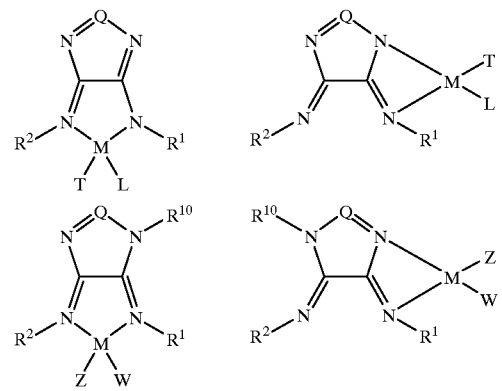

wherein M represents the transition metal, and Q, T, L, W, Z, $R^1$, $R^2$ and $R^{10}$ represent functional groups.

86 Claims, No Drawings

FOREIGN PATENT DOCUMENTS

| | | |
|---|---|---|
| WO 98/30610 | 7/1998 | (WO) . |
| WO 98/30612 | 7/1998 | (WO) . |
| WO 98/37110 | 8/1998 | (WO) . |
| WO 98/40374 | 9/1998 | (WO) . |
| WO 98/40420 | 9/1998 | (WO) . |
| WO 98/42440 | 10/1998 | (WO) . |
| WO 98/42664 | 10/1998 | (WO) . |
| WO 98/42665 | 10/1998 | (WO) . |
| WO 98/45342 | 10/1998 | (WO) . |
| WO 98/47933 | 10/1998 | (WO) . |
| WO 98/47934 | 10/1998 | (WO) . |
| WO 98/49208 | 11/1998 | (WO) . |
| WO 98/56832 | 12/1998 | (WO) . |
| WO 98/56837 | 12/1998 | (WO) . |
| WO 98/56839 | 12/1998 | (WO) . |
| WO 99/02472 | 1/1999 | (WO) . |
| WO 99/05189 | 2/1999 | (WO) . |
| WO 99/09078 | 2/1999 | (WO) . |

OTHER PUBLICATIONS

Peter Langer et al., "Regioselective Cyclizations of Delocalized 1,3–Amide Dianions with Oxalic Acid Dielectrophiles", *Liebigs Ann./Recueil* 1997, 2553–2561.

Jurgen Fabian, et al., "5–Ring Cycloamidines—Novel Colored Heterocycles with Unusual Properties. II [5] Molecular and Electronic Structure", *J. prakt. Chem* 339 (1997) 735–741.

Peer Fehling et al., "Ion Pairing and Cyclization on Coordinatively Bound Oxalamidines", *Cham. Ber.* 1995, 128, 405–412.

Gregory F. Schmidt et al., "Implications of Three–Center, Two–Electron M–H–C Bonding for Related Alkyl Migration Reactions: Design and Study of an Ethylene Polymerization Catalyst", *J. Am. Chem. Soc.* 1985, 1443–1444.

K.A. Ostoja Starzewski et al., "Control of the Molecular Weight of Polyethene in Syntheses with Bis(ylide)nickel Catalysts", *Agnew. Chem. Int. Ed. Engl.* 26 (1987) No. 1, 63–64.

Lynda K. Johnson et al., "New Pd(II)–and Ni(II)–Based Catalysts for Polymerization of Ethylene and α–Olefins", *J. Am. Chem. Soc.* 1995, 117, 6414–6415.

Marcel Peuckart et al., "A New Nickel Complex for the Oligomerization of Ethylene", *Organometallics* 1983, 2, 594–597.

Günther Wilke, "Contributions to Organo–Nickel Chemistry", *Angewandte Chemie*, International Edition in English, vol. 27, No. 1, Jan. 1988, pp. 185–206.

Christopher M. Killian et al., "Preparation of Linear α–Olefins Using Cationic Nickel (II) α–Diimine Catalysts", *Organometallics* 1997, 16, 2005–2007.

Christopher M. Killian et al., "Living Polymerization of α–Olefins Using NiII–α–Diimine Catalysts. Synthesis of New Block Polymers Based on α–Olefins", *J. Am. Chem. Soc.* 1996, 118, 11664–11665.

Stephan J. McLain et al., "Communications to the Editor, Addition Polymerization of Cyclopentene with Nickel and Palladium Catalysts", *Macromolecules* 1998, 31, 6705–6707.

Wilhelm Keim et al., "Novel Nickel–and Palladium–Complexes with Aminobis(imino)phosphorane Ligands for the Polymerization of Ethylene", *Chem. Int. Ed. Engl.* 20 (1981) No. 1, 116–117.

M. Döring, et al., "Nitrogen Derivatives of Oxalic Acid as New Complexing Agents", *Z. anorg. allg. Chem.* 620 (1994) 551–560.

Volker Michael Möhring et al., "Novel Polymerization of α–Olefins with the Catalysts System Nickel/Aminobis(imino)phosphorane", *Agnew. Chem. Int. Ed. Engl.* 24 (1985) No. II, 1001–1003.

Stefan Mecking et al., "Mechanistic Studies of the Palladium–Catalyzed Copolymerization of Ethylene and α–Olefins with Methyl Acrylate", *J. Am. Chem. Soc.* 1988, 120, 888–889.

Lynda K. Johnson et al., "Copolymerization of Ethylene and Propylene with Functionalized Vinyl Monomers by Palladium(II) Catalysts", *J. Am. Chem. Soc.* 1996, 118, 267–268.

Christopher M. Killian, "Ni(II) Based Catalysts for the Polymerization and Copolymerization of Olefins: A New Generation of Polyolefins," The University of North Carolina at Chapel Hill (1996), Doctoral Dissertation.

GROUP 8-10 TRANSITION METAL OLEFIN POLYMERIZATION CATALYSTS

CROSS-REFERENCE TO RELATED APPLICATIONS

This is a continuation-in-part application of application Ser. No. 09/028,316 ("the '316 application") filed on Feb. 24, 1998, now abandoned, the entire content of which is hereby incorporated by reference, which claims the benefit under 35 U.S.C. §119(e) of Provisional Application Serial No. 60/044,691, filed on Apr. 18, 1997, and Provisional Application Ser. No. 60/045,333, filed on May 1, 1997, and Provisional Application Serial No. 60/045,355, filed on May 2, 1997; the entire contents of which are also hereby incorporated by reference.

FIELD OF THE INVENTION

The present invention is directed to olefin polymers, such as polyethylene, polypropylene, and copolymers of ethylene and propylene, and to the preparation of such olefin polymers. These polymers include homopolymers of olefins, as well as copolymers of different olefins. The present invention is also directed to processes of making these olefin polymers, which typically use a transition metal complex, in which the transition metal is a Group 8-10 metal, as the polymerization catalyst. The polymers have a wide variety of applications, including use as packaging materials and adhesives. In addition, the present invention is directed to catalysts for the polymerization of olefins.

BACKGROUND OF THE INVENTION

Olefin polymers are used in a wide variety of products, from sheathing for wire and cable to film. Olefin polymers are used, for instance, in injection or compression molding applications, in extruded films or sheeting, as extrusion coatings on paper, for example photographic paper and digital recording paper, and the like. Improvements in catalysts have made it possible to better control polymerization processes, and, thus, influence the properties of the bulk material. Increasingly, efforts are being made to tune the physical properties of plastics for lightness, strength, resistance to corrosion, permeability, optical properties, and the like, for particular uses. Chain length, polymer branching and functionality have a significant impact on the physical properties of the polymer. Accordingly, novel catalysts are constantly being sought in attempts to obtain a catalytic process which permits more efficient and better controlled polymerization of olefins.

Conventional polyolefins are prepared by a variety of polymerization techniques, including homogeneous and heterogeneous polymerizations. Certain transition metal catalysts, such as those based on titanium compounds (e.g., $TiCl_3$ or $TiCl_4$) in combination with organoaluminum cocatalysts, are used to make linear and linear low density polyethylenes as well as poly-α-olefins such as polypropylene. These so-called "Ziegler-Natta" catalysts are quite sensitive to oxygen and are ineffective for the copolymerization of nonpolar and polar monomers.

Recent advances in non-Ziegler-Natta olefin polymerization catalysis include the following:

L. K. Johnson et al., WO Patent Application 96/23010, disclose the polymerization of olefins using cationic nickel, palladium, iron, and cobalt complexes containing diimine and bisoxazoline ligands. This document also describes the polymerization of ethylene, acyclic olefins, and/or selected cyclic olefins and optionally selected unsaturated acids or esters such as acrylic acid or alkyl acrylates to provide olefin homopolymers or copolymers.

European Patent Application No. 381,495 describes the polymerization of olefins using palladium and nickel catalysts which contain selected bidentate phosphorous containing ligands.

L. K. Johnson et al., *J. Am. Chem. Soc.*, 1995, 117, 6414, describe the polymerization of olefins such as ethylene, propylene, and 1-hexene using cationic α-diimine-based nickel and palladium complexes. These catalysts have been described to polymerize ethylene to high molecular weight branched polyethylene. In addition to ethylene, Pd complexes act as catalysts for the polymerization and copolymerization of olefins and methyl acrylate.

G. F. Schmidt et al., *J. Am. Chem. Soc.*, 1985, 107, 1443, describe a cobalt(III) cyclopentadienyl catalytic system having the structure $[C_5Me_5(L)CoCH_2CH_2\text{-}\mu\text{-}H]^+$, which provides for the "living" polymerization of ethylene.

M. Brookhart et al., *Macromolecules*, 1995, 28, 5378, disclose using such "living" catalysts in the synthesis of end-functionalized polyethylene homopolymers.

U. Klabunde, U.S. Pat. Nos. 4,906,754, 4,716,205, 5,030,606, and 5,175,326, describes the conversion of ethylene to polyethylene using anionic phosphorous/oxygen donors ligated to Ni(II). The polymerization reactions were run between 25 and 100° C. with modest yields, producing linear polyethylene having a weight-average molecular weight ranging between 8K and 350K. In addition, Klabunde describes the preparation of copolymers of ethylene and functional group containing monomers.

M. Peuckert et al., *Organomet.*, 1983, 2(5), 594, disclose the oligomerization of ethylene using phosphine/carboxylate donors ligated to Ni(II), which showed modest catalytic activity (0.14 to 1.83 TO/s). The oligomerizations were carried out at 60 to 95° C. and 10 to 80 bar ethylene in toluene, to produce linear α-olefins.

R. E. Murray, U.S. Pat. Nos. 4,689,437 and 4,716,138, describes the oligomerization of ethylene using phosphinelsulfonate donors ligated to Ni(II). These complexes show catalyst activities approximately 15 times greater than those reported with phosphine/carboxylate analogs.

W. Keim et al., *Angew. Chem. Int. Ed. Eng.*, 1981, 20, 116, and V. M. Mohring et al., *Angew. Chem. Int. Ed. Eng.*, 1985, 24, 1001, disclose the polymerization of ethylene and the oligomerization of α-olefins with aminobis(imino) phosphorane nickel catalysts.

G. Wilke, Angew. *Chem. Inmt. Ed. Engl.*, 1988, 27, 185, describes a nickel allyl phosphine complex for the polymerization of ethylene.

K. A. O. Starzewski et al., *Angew. Chem. Int. Ed. Engl.*, 1987, 26, 63, and U.S. Pat. No. 4,691,036, describe a series of bis(ylide) nickel complexes, used to polymerize ethylene to provide high molecular weight linear polyethylene.

WO Patent Application 97/02298 discloses the polymerization of olefins using a variety of neutral N, O, P, or S donor ligands, in combination with a nickel(0) compound and an acid.

Brown et al., WO 97/17380, describes the use of Pd α-diimine catalysts for the polymerization of olefms including ethylene in the presence of air and moisture.

Fink et al., U.S. Pat. No. 4,724,273, have described the polymerization of α-olefins using aminobis(imino) phosphorane nickel catalysts and the compositions of the resulting poly(α-olefins).

Additional recent developments are described by Sugimura et al., in JP 96-84344, JP 96-84343, and WO 9738024, and by Yorisue et al., in JP 96-70332. Moreover, the University of North Carolina and Du Pont have reported the polymerization of olefins using neutral nickel catalysts in WO 9830609 and WO 9830610.

Notwithstanding these advances in non-Ziegler-Natta catalysis, there remains a need for efficient and effective Group 8–10 transition metal catalysts for effecting polymerization of olefins. In addition, there is a need for novel methods of polymerizing olefins employing such effective Group 8–10 transition metal catalysts. In particular, there remains a need for Group 8–10 transition metal olefin polymerization catalysts with both improved temperature stability and functional group compatibility. Further, there remains a need for a method of polymerizing olefins utilizing effective Group 8–10 transition metal catalysts in combination with a Lewis acid so as to obtain a catalyst that is more active and more selective.

SUMMARY OF THE INVENTION

The present invention provides a process for the production of polyolefins, comprising: contacting, at a temperature from about –100° C. to about 200° C., one or more monomers of the formula RCH=CHR$^3$ with a catalyst comprising (i) a transition metal complex of formula I or Ia, and, optionally, (ii) a neutral Lewis acid;

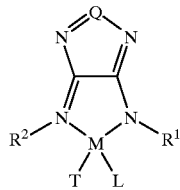

I

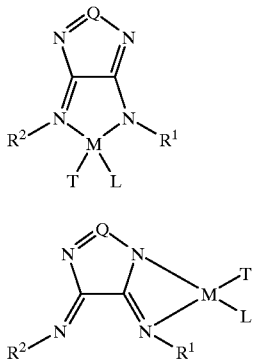

Ia wherein R and R$^3$ are each, independently, hydrogen, hydrocarbyl or substituted hydrocarbyl and may be linked to form a cyclic olefin;

R$^1$ and R$^2$ are each independently hydrocarbyl, substituted hydrocarbyl, or silyl;

Q is (i) C—R$^4$, where R$^4$ is hydrocarbyl, substituted hydrocarbyl, heteroatom connected hydrocarbyl, or heteroatom connected substituted hydrocarbyl, (ii) P(NH$_2$)$_2$, or (iii) S(NH)(NH$_2$) or S(O)(OH);

L is a monoolefin or a neutral Lewis base that can be displaced by a monoolefin;

T is hydrogen, hydrocarbyl or substituted hydrocarbyl, or may be taken together with L to form a π-allyl group; and M is Ni(II), Pd(II), Co(II) or Fe(II). The catalyst may be in supported or unsupported form.

This invention also provides a compound of formula I or Ia:

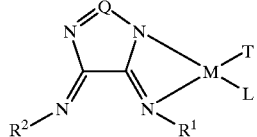

I

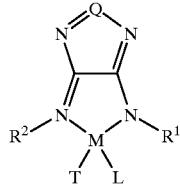

Ia wherein R$^1$ and R$^2$ are each independently hydrocarbyl, substituted hydrocarbyl, or silyl;

Q is (i) C—R$^4$, where R$^4$ is hydrocarbyl, substituted hydrocarbyl, heteroatom connected hydrocarbyl, or heteroatom connected substituted hydrocarbyl, (ii) P(NH$_2$)$_2$, or (iii) S(NH)(NH$_2$) or S(O)(OH);

L is a monoolefin or a neutral Lewis base that can be displaced by a monoolefin;

T is hydrogen, hydrocarbyl or substituted hydrocarbyl, or may be taken together with L to form a π-allyl group; and M is Ni(II), Pd(II), Co(II) or Fe(II).

This invention also provides a catalyst composition which comprises (i) a compound of formula I or Ia, and optionally, (ii) a neutral Lewis acid;

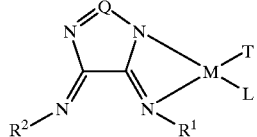

I

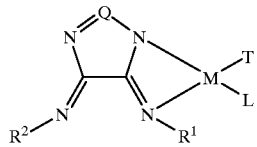

Ia wherein R$^1$ and R$^2$ are each independently hydrocarbyl, substituted hydrocarbyl, or silyl;

Q is (i) C—R$^4$, where R$^4$ is hydrocarbyl, substituted hydrocarbyl, heteroatom connected hydrocarbyl, or heteroatom connected substituted hydrocarbyl, (ii) P(NH$_2$)$_2$, or (iii) S(NH)(NH$_2$) or S(O)(OH);

L is a mononoolefin or a neutral Lewis base that can be displaced by a monoolefin;

T is hydrogen, hydrocarbyl or substituted hydrocarbyl, or may be taken together with L to form a π-allyl group; and M is Ni(II), Pd(II), Co(II) or Fe(II). The catalyst may be in supported or unsupported form.

The present invention further relates to process for the preparation of a supported catalyst, comprising: contacting (i) a compound of formula I or Ia, (ii) silica, and (iii) a neutral Lewis acid selected from the group consisting of B(C$_6$F$_5$)$_3$, methylaluminoxane, BPh$_3$, and B(3,5-(CF$_3$)C$_6$H$_3$)$_3$;

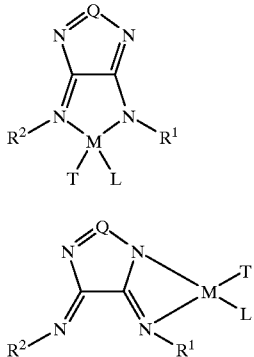

I

Ia wherein R$^1$ and R$^2$ are each independently hydrocarbyl, substituted hydrocarbyl, or silyl;

Q is (i) C—R$^4$, where R$^4$ is hydrocarbyl, substituted hydrocarbyl, heteroatom connected hydrocarbyl, or heteroatom connected substituted hydrocarbyl, (ii) P(NH$_2$)$_2$, or (iii) S(NH)(NH$_2$) or S(O)(OH);

L is a monoolefin or a neutral Lewis base that can be displaced by a monoolefin;

T is hydrogen, hydrocarbyl or substituted hydrocarbyl, or may be taken together with L to form a π-allyl group; and M is Ni(II), Pd(II), Co(II) or Fe(II).

The present invention also provides a process for the polymerization of olefms, comprising: contacting, at a temperature from about −100° C. to about 200° C., one or more monomers of the formula RCH═CHR$^3$ with a catalyst comprising the reaction product of (i) a compound of the formula II, or tautomers thereof, (ii) a suitable precursor selected from the group consisting of Ni, Pd, Co, and Fe compounds, and, optionally, (iii) a neutral Lewis acid;

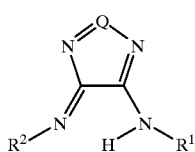

II wherein R and R$^3$ are each, independently, hydrogen, hydrocarbyl or fluoroalkyl and may be linked to form a cyclic olefin;

R$^1$ and R$^2$ are each independently hydrocarbyl, substituted hydrocarbyl, or silyl; and Q is (i) C—R$^4$, wherein R$^4$ is hydrocarbyl, substituted hydrocarbyl, heteroatom connected hydrocarbyl, or heteroatom connected substituted hydrocarbyl, (ii) P(NH$_2$)$_2$, or (iii) S(NH)(NH$_2$) or S(O)(OH). The catalyst may be in supported or unsupported form.

The invention also provides a compound of formula II, or tautomers thereof:

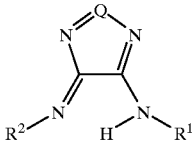

II wherein R$^1$ and R$^2$ are both sterically hindered aryl rings; and

Q is (i) C—R$^4$, where R$^4$ is hydrocarbyl, substituted hydrocarbyl, heteroatom connected hydrocarbyl, or heteroatom connected substituted hydrocarbyl, (ii) P(NH$_2$)$_2$, or (iii) S(NH)(NH$_2$) or S(O)(OH).

The present invention further provides a catalyst composition which comprises the reaction product of (i) a compound of formula II, or tautomers thereof, (ii) a suitable precursor selected from the group consisting of Ni, Pd, Co, and Fe compounds, and, optionally, (iii) a neutral Lewis acid;

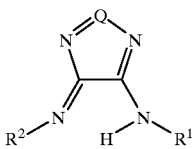

II wherein R$^1$ and R$^2$ are both sterically hindered aryl rings; and

Q is (i) C—R$^4$, where R$^4$ is hydrocarbyl, substituted hydrocarbyl, heteroatom connected hydrocarbyl, or heteroatom connected substituted hydrocarbyl, (ii) P(NH$_2$)$_2$, or (iii) S(NH)(NH$_2$) or S(O)(OH). The catalyst may be in supported or unsupported form.

The invention further provides a process for the preparation of a supported catalyst, comprising: contacting (i) a compound of the formula II, or tautomers thereof, (ii) a suitable precursor selected from the group consisting of Ni, Pd, Co, and Fe compounds, (iii) a neutral Lewis acid selected from the group consisting of B(C$_6$F$_5$)$_3$, methylaluminoxane, BPh$_3$, and B(3,5-(CF$_3$)C$_6$H$_3$)$_3$, and (iv) silica;

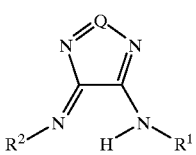

II

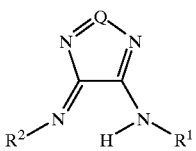

wherein R and R$^3$ are each, independently, hydrogen, hydrocarbyl or fluoroalkyl and may be linked to form a cyclic olefin;

R$^1$ and R$^2$ are each independently hydrocarbyl, substituted hydrocarbyl, or silyl; and Q is (i) C—R$^4$, wherein R$^4$ is hydrocarbyl, substituted hydrocarbyl, heteroatom connected hydrocarbyl, or heteroatom connected substituted hydrocarbyl, (ii) P(NH$_2$)$_2$, or (iii) S(NH)(NH) or S(O)(OH).

The present invention also provides a process for the polymerization of olefins, comprising: contacting one or more monomers of the formula RCH═CHR$^3$ with a catalyst comprising the reaction product of (i) a binucleating or multinucleating ligand complexed to a Group 8–10 transition metal M and (ii) one or more neutral Lewis acids, wherein the Lewis acid or acids are bound to one or more heteroatoms which are π-conjugated to the donor atom or atoms bound to the transition metal M; and wherein R and R³ each, independently, represent a hydrogen, a hydrocarbyl, a fluoroalkyl, or may be linked to form a cyclic olefin. The catalyst may be in supported or unsupported form.

The invention also provides a catalyst composition comprising the reaction product of (i) a Group 8–10 transition metal M, (ii) one or more neutral Lewis acids, and (iii) a binucleating or multinucleating compound of the formula II:

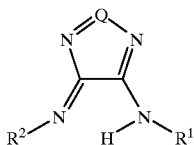

II wherein the Lewis acid or acids are bound to one or more heteroatoms which are π-conjugated to the donor atom or atoms bound to the transition metal M;

R¹ and R² are both sterically hindered aryl rings; and

Q is (i) C—R⁴, where R⁴ is hydrocarbyl, substituted hydrocarbyl, heteroatom connected hydrocarbyl, or heteroatom connected substituted hydrocarbyl, (ii) P(NH₂)₂, or (iii) S(NH)(NH₂) or S(O)(OH). The catalyst may be in supported or unsupported form.

The invention further provides a process for the polymerization of olefins, comprising: contacting, at a temperature from about −100° C. to about 200° C., one or more monomers of the formula RCH=CHR³, with a catalyst comprising the reaction product of (i) an anionic compound of the formula III, (ii) a suitable divalent metal precursor selected from the group consisting of Ni(II), Pd(II), Co(II), and Fe(II) compounds, and, optionally, (iii) a neutral Lewis acid;

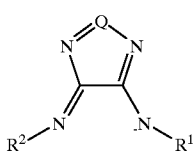

III wherein R and R³ are each, independently, hydrogen, hydrocarbyl or fluoroalkyl and may be linked to form a cyclic olefin;

R¹ and R² are each independently hydrocarbyl, substituted hydrocarbyl, or silyl; and Q is C—R⁴, where R⁴ is hydrocarbyl, substituted hydrocarbyl, heteroatom connected hydrocarbyl, heteroatom connected substituted hydrocarbyl, or O—Si (tert-butyl)(CH₃)₂. The catalyst may be in supported or unsupported form.

The present invention also provides a process for the production of polyolefins, comprising: contacting, at a temperature from about −100° C. to about 200° C., one or more monomers of the formula RCH=CHR³ with a catalyst comprising (i) a transition metal complex of formula V or Va, or tautomers thereof, and, optionally, (ii) a neutral Lewis acid;

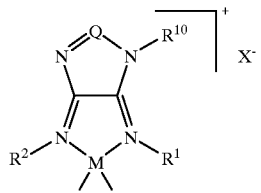

V

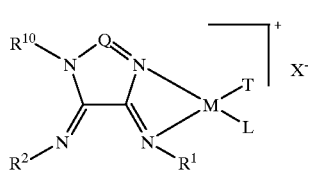

Va wherein R and R³ are each, independently, hydrogen, hydrocarbyl or substituted hydrocarbyl and may be linked to form a cyclic olefin;

R¹ and R² are each independently hydrocarbyl, substituted hydrocarbyl, or silyl;

Q is (i) C—R⁴, where R⁴ is hydrocarbyl, substituted hydrocarbyl, heteroatom connected hydrocarbyl, or heteroatom connected substituted hydrocarbyl, (ii) P(NH₂)₂, or (iii) S(NH)(NH₂) or S(O)(OH);

L is a monoolefin or a neutral Lewis base that can be displaced by a monoolefin;

T is hydrogen, hydrocarbyl or substituted hydrocarbyl, or may be taken together with L to form a π-allyl group;

M is Ni(II), Pd(II), Co(II) or Fe(II);

R¹⁰ is hydrogen, hydrocarbyl, substituted hydrocarbyl, or silyl; and

X is a weakly coordinating anion. The catalyst may be in supported or unsupported form.

The invention further provides a compound of formula V or Va, or tautomers thereof:

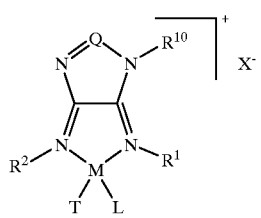

V

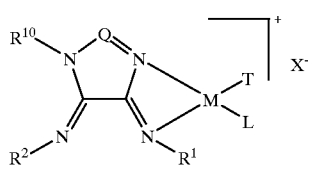

Va

R¹ and R² are each independently hydrocarbyl, substituted hydrocarbyl, or silyl;

Q is (i) C—R⁴, where R⁴ is hydrocarbyl, substituted hydrocarbyl, heteroatom connected hydrocarbyl, or heteroatom connected substituted hydrocarbyl, (ii) P(NH₂)₂, or (iii) S(NH)(NH₂) or S(O)(OH);

L is a monoolefin or a neutral Lewis base that can be displaced by a monoolefin;

T is hydrogen, hydrocarbyl or substituted hydrocarbyl, or may be taken together with L to form a π-allyl group;

M is Ni(II), Pd(II), Co(II) or Fe(II);

$R^{10}$ is hydrogen, hydrocarbyl, substituted hydrocarbyl, or silyl; and

X is a weakly coordinating anion.

The present invention also provides a catalyst composition which comprises (i) a transition metal complex of formula V or Va, or tautomers thereof, and, optionally, (ii) a neutral Lewis acid;

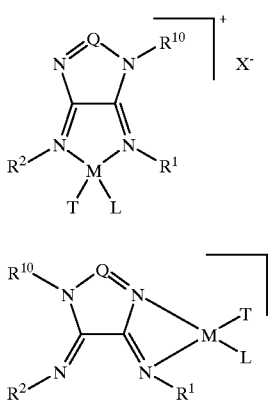

$R^1$ and $R^2$ are each independently hydrocarbyl, substituted hydrocarbyl, or silyl;

Q is (i) C—$R^4$, where $R^4$ is hydrocarbyl, substituted hydrocarbyl, heteroatom connected hydrocarbyl, or heteroatom connected substituted hydrocarbyl, (ii) P(NH$_2$)$_2$, or (iii) S(NH)(NH$_2$) or S(O)(OH);

L is a monoolefin or a neutral Lewis base that can be displaced by a monoolefin;

T is hydrogen, hydrocarbyl or substituted hydrocarbyl, or may be taken together with L to form a π-allyl group;

M is Ni(II), Pd(II), Co(II) or Fe(II);

$R^{10}$ is hydrogen, hydrocarbyl, substituted hydrocarbyl, or silyl; and

X is a weakly coordinating anion. The catalyst may be in supported or unsupported form.

The invention further provides a process for the production of polyolefins, comprising: contacting, at a temperature from about −100° C. to about 200° C., one or more monomers of the formula RCH=CHR$^3$ with a catalyst comprising (i) a transition metal complex of formula VI or VIa, and (ii) a neutral Lewis acid;

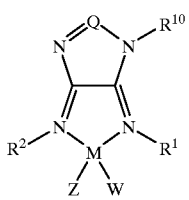

VI

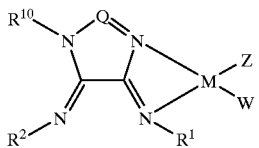

VIa wherein R and $R^3$ are each, independently, hydrogen, hydrocarbyl or substituted hydrocarbyl and may be linked to form a cyclic olefin;

$R^1$ and $R^2$ are each independently hydrocarbyl, substituted hydrocarbyl, or silyl;

Q is (i) C—$R^4$, where $R^4$ is hydrocarbyl, substituted hydrocarbyl, heteroatom connected hydrocarbyl, or heteroatom connected substituted hydrocarbyl, (ii) P(NH$_2$)$_2$, or (iii) S(NH)(NH$_2$) or S(O)(OH);

Z and W each independently represent Cl, Br, I, methyl, or H;

M is Ni(II), Pd(II), Co(II) or Fe(II); and $R^{10}$ is hydrogen, hydrocarbyl, substituted hydrocarbyl, or silyl. The catalyst may be in supported or unsupported form.

The present invention also provides a compound of formula VI or VIa:

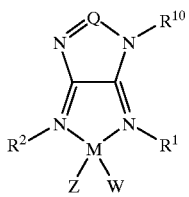

VI

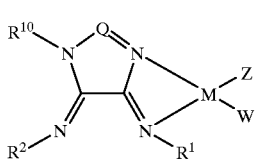

VIa $R^1$ and $R^2$ are each independently hydrocarbyl, substituted hydrocarbyl, or silyl;

Q is (i) C—$R^4$, where $R^4$ is hydrocarbyl, substituted hydrocarbyl, heteroatom connected hydrocarbyl, or heteroatom connected substituted hydrocarbyl, (ii) P(NH$_2$)$_2$, or (iii) S(NH)(NH$_2$) or S(O)(OH);

Z and W each independently represent Cl, Br, I, methyl, or H;

M is Ni(II), Pd(II), Co(II) or Fe(II); and $R^{10}$ is hydrogen, hydrocarbyl, substituted hydrocarbyl, or silyl.

Finally, the present invention provides a catalyst composition which comprises (i) a transition metal complex of formula VI or VIa, and (ii) a neutral Lewis acid;

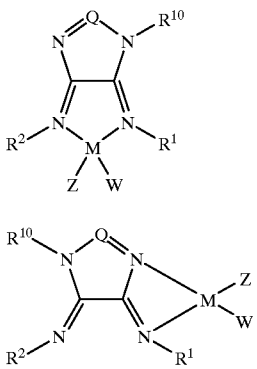

VI

VIa

R¹ and R² are each independently hydrocarbyl, substituted hydrocarbyl, or silyl;

Q is (i) C—R⁴, where R⁴ is hydrocarbyl, substituted hydrocarbyl, heteroatom connected hydrocarbyl, or heteroatom connected substituted hydrocarbyl, (ii) P(NH$_2$)$_2$, or (iii) S(NH)(NH$_2$) or S(O)(OH);

Z and W each independently represent Cl, Br, I, methyl, or H;

M is Ni(II), Pd(II), Co(II) or Fe(II); and

R¹⁰ is hydrogen, hydrocarbyl, substituted hydrocarbyl, or silyl. The catalyst may be in supported or unsupported form.

DETAILED DESCRIPTION OF THE INVENTION

In this disclosure, certain chemical groups and compounds are described by certain terms, symbols, and formulas. No specific stereochemistry is implied or intended by the formulas. Symbols ordinarily used to denote elements in the Periodic Table take their ordinary meaning, unless otherwise specified. The terms are defined as follows:

Examples of neutral Lewis bases include, but are not limited to, (i) ethers, for example, diethyl ether or tetrahydrofuran, (ii) organic nitrites, for example, acetonitrile, (iii) organic sulfides, for example, dimethylsulfide, or (iv) monoolefins, for example, ethylene, hexene or cyclopentene.

Examples of neutral Lewis acids include, but are not limited to, methylaluminoxane (hereinafter "MAO") and other aluminum sesquioxides, R⁷$_3$Al, R⁷$_2$AlCl, R⁷AlCl$_2$ (where R⁷ is alkyl), organoboron compounds, boron halides, B(C$_6$F$_5$)$_3$, BPh$_3$, and B(3,5-(CF$_3$)C$_6$H$_3$)$_3$.

Examples of ionic compounds comprising a cationic Lewis acid include: R⁹$_3$Sn[BF$_4$] (where R⁹ is hydrocarbyl), MgCl$_2$, and H⁺X⁻, where X⁻ is a weakly coordinating anion.

The term "weakly coordinating anion" is well known in the art and generally refers to a large bulky anion capable of delocalization of the negative charge of the anion. Suitable weakly coordinating anions include, but are not limited to, PF$_6$⁻, BF$_4$⁻, SbF$_6$⁻, (Ph)$_4$B⁻ wherein Ph=phenyl, and ⁻BAr$_4$ wherein ⁻BAr$_4$=tetrakis[3,5-bis(trifluoromethyl)phenyl]borate. The coordinating ability of such anions is known and described in the literature (e.g., S. Strauss et al., *Chem. Rev.*, 1993, 93, 927).

A "sterically hindered aryl" means (i) a phenyl ring with hydrocarbyl, substituted hydrocarbyl, F, Cl, Br or silyl substituents at both the 2- and 6-positions, optionally substituted elsewhere with hydrocarbyl, substituted hydrocarbyl, F, Cl, Br, silyl, hydroxy, methoxy, nitro, cyano, phenylsulfonyl, CO$_2$Me, CO$_2$H, C(O)CH$_3$, CF$_3$, or fluoroalkyl substituents, (ii) a 2-substituted napth-1-yl ring, optionally substituted elsewhere with hydrocarbyl, substituted hydrocarbyl, F, Cl, Br, silyl, hydroxy, methoxy, nitro, cyano, phenylsulfonyl, CO$_2$Me, CO$_2$H, C(O)CH$_3$, CF$_3$, or fluoroalkyl substituents, (iii) a 9-anthracenyl or a 1,2,3,4,5,6,7,8-octahydro-9-anthracenyl ring, optionally substituted elsewhere with hydrocarbyl, substituted hydrocarbyl, F, Cl, Br, silyl, hydroxy, methoxy, nitro, cyano, phenylsulfonyl, CO$_2$Me, CO$_2$H, C(O)CH$_3$, CF$_3$, or fluoroalkyl substituents, or (iv) an aromatic substituted hydrocarbyl with steric properties functionally equivalent (in the context of this invention) to one or more of the following sterically hindered aryls: 2,6-dimethylphenyl, 2,4,6-trimethylphenyl, 2,6-diisopropylphenyl, 2,6-dimethyl-4-nitrophenyl, 2,6-dimethyl-4-phenylsulfonylphenyl, 2-isopropyl-6-methylphenyl, 2,6-bis(trifluoromethyl)phenyl, 2,6-dimethyl-4-methoxyphenyl, 2-methylnapth-1-yl, 9-anthracenyl, 1,2,3,4,5,6,7,8-octahydro-9-anthracenyl, 2,6-diclorophenyl, 2,6dibromophenyl, 2-tert-butyl-6-methylphenyl, 2-trimethylsilylnapth-1-yl, 2-chloro-6-methylphenyl, 4-cyano-2,6-dimethylphenyl, 2,6-diisopropyl-4-methoxyphenyl, 2,4,6-tri-tert-butylphenyl, 2-chloro4-tert-butylphenyl, 2-tert-butylphenyl, and 2-trimethylsilylphenyl.

A "hydrocarbyl" group means a linear, branched or cyclic group which contains only carbon and hydrogen atoms. Examples include: C$_1$–C$_{20}$ alkyl; C$_1$–C$_{20}$ alkyl substituted with one or more groups selected from C$_1$–C$_{20}$ alkyl, C$_3$–C$_8$ cycloalkyl or aryl; C$_3$–C$_8$ cycloalkyl; C$_3$–C$_8$ cycloalkyl substituted with one or more groups selected from C$_1$–C$_{20}$ alkyl, C$_3$–C$_8$ cycloalkyl or aryl; C$_6$–C$_{14}$ aryl; and C$_6$–C$_{14}$ aryl substituted with one or more groups selected from C$_1$–C$_{20}$ alkyl, C$_3$–C$_8$ cycloalkyl or aryl; where the term "aryl" preferably denotes a phenyl, napthyl, or anthracenyl group.

Examples of groups useful as the group Q include (i) C-aryl, where aryl is phenyl, pentafluorophenyl, or phenyl substituted with F, Cl, Br, methoxy, cyano, nitro, CO$_2$H, CF$_3$, fluoroalkyl, or phenylsulfonyl, (ii) C-tert-butyl, C—CF$_3$, or C-fluoroalkyl, (iii) C—S—R⁵ or C—O—R⁵, where R⁵ is C$_1$–C$_{20}$ alkyl, silyl, phenyl, or phenyl substituted with F, Cl, Br, CF$_3$, fluoroalkyl, CO$_2$H, methoxy, cyano, nitro, or phenylsulfonyl, (iv) C-silyl, (v) P(NH$_2$)$_2$, or (vi) S(NH)(NH$_2$) or S(O)(OH).

A "silyl" group refers to a SiR⁶$_3$ group where Si is silicon and R⁶ is hydrocarbyl or substituted hydrocarbyl or silyl, as in Si(SiR⁶$_3$)$_3$.

A "heteroatom" refers to an atom other than carbon or hydrogen. Preferred heteroatoms include oxygen, nitrogen, phosphorus, sulfur, selenium, silicon, arsenic, chlorine, bromine, and fluorine.

A "fluoroalkyl" as used herein refers to a C$_1$–C$_{20}$ alkyl group substituted by one or more fluorine atoms.

A "substituted hydrocarbyl" refers to a hydrocarbyl substituted with one or more heteroatoms. Examples include: 2,6-dimethyl-4-methoxyphenyl, 2,6-diisopropyl-4-methoxyphenyl, 4-cyano-2,6-dimethylphenyl, 2,6-dimethyl4-nitrophenyl, 2,6-difluorophenyl, 2,6-dibromophenyl, 2,6-dichlorophenyl, 4-methoxycarbonyl-2,6-dimethylphenyl, 2-tert-butyl-6-chlorophenyl, 2,6-dimethyl-4-phenylsulfonylphenyl, 2,6-dimethyl-4-trifluoromethylphenyl, 2,6-dimethyl4-hydroxyphenyl, 9-hydroxyanthr-10yl, 2-chloronapth-1-yl, 4-methoxyphenyl, 4-nitrophenyl, 9-nitroanthr-10-yl, CH$_2$OCH$_3$, cyano, trifluoromethyl, or fluoroalkyl.

A "heteroatom connected hydrocarbyl" refers to a group of the type Z-(hydrocarbyl), where Z is a divalent heteroatom, preferably O or S, or Z-(hydrocarbyl)$_2$, where Z is a trivalent heteroatom, preferably N. Examples include: OCH$_3$, OPh, N(CH$_3$)$_2$, SCH$_3$, or SPh.

A "heteroatom connected substituted hydrocarbyl" refers to a group of the type Z-(substituted hydrocarbyl), where Z is a divalent heteroatom, preferably O or S, or Z-(substituted hydrocarbyl)$_2$, where Z is a trivalent heteroatom, preferably N. Examples include: OCH$_2$CF$_3$, SC(O)CH$_3$, and 1-morpholinyl.

A "mono-olefin" refers to a hydrocarbon containing one carbon-carbon double bond.

A "suitable precursor" refers to a zerovalent or divalent transition metal compound which may be combined with compound II, and optionally a neutral Lewis acid, to form an active olefin polymerization catalyst. Examples of suitable precursors include: bis(1,5-cyclooctadiene)nickel(0) and bis[(1, 2, 3-η$^3$-2-propenyl)nickel(II)].

A "suitable divalent metal precursor" refers to a divalent transition metal compound which may be combined with compound III, and optionally a neutral Lewis acid, to form an active olefin polymerization catalyst. Examples include: (1,2-dimethoxyethane)nickel(II) dibromide, bis[(μ-chloro)(1, 2, 3-η$^3$-2-propenyl)nickel(II)], bis[(μ-chloro)(1, 2, 3-η$^3$-2-propenyl)palladium(II)], bis[(μ-chloro)(1, 2, 3-η$^3$-1-trimethylsilyloxy-2-propenyl)nickel(II)], CoBr$_2$, FeBr$_2$.

A "π-allyl" group refers to a monoanionic group with three sp$^2$ carbon atoms bound to a metal center in a η$^3$-fashion. Any of the three sp$^2$ carbon atoms may be substituted with a hydrocarbyl, substituted hydrocarbyl, heteroatom connected hydrocarbyl, heteroatom connected substituted hydrocarbyl, or O-silyl group. Examples of π-allyl groups include:

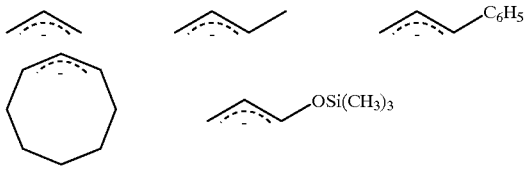

The term "polymer" as used herein is meant a species comprised of monomer units and having a degree of polymerization (DP) of ten or higher.

As used herein, the terms "monomer" and "olefin monomer" refer to the olefin or other monomer compound before it has been polymerized; the term "monomer units" refers to the moieties of a polymer that correspond to the monomers after they have been polymerized.

Described herein is a process for the polymerization of olefins. Preferred olefins include ethylene and a-olefins such as propylene, 1-butene, 1-hexene, 1-octene, and cyclic olefins such as cyclopentene.

When the polymerizations are conducted in the liquid phase, the liquid phase may include solvent or neat monomer. The molar ratio of neutral Lewis acid to transition metal complex can be from 0 to 10000, preferably 0 to 100, more preferably 0 to 10. The pressure at which the ethylene polymerizations and copolymerizations take place can be from 1 atmosphere to 1000 atmospheres, preferably 1 to 100 atmospheres.

While not wishing to be bound by theory, the present inventors believe that the neutral Lewis acid may be acting to further activate the catalysts disclosed herein via coordination to one or more of those heteroatoms which are not directly bound to the transition metal M, but which are π-conjugated to the nitrogens which are bound to the transition metal M. Substituents which contain additional Lewis basic groups, including, but not limited to, methoxy groups, positioned so as to further promote the binding of the Lewis acid at such π-conjugated heteroatoms, are also included in this invention. A non-limiting example of secondary Lewis acid binding would include formula IV or IVa as follows:

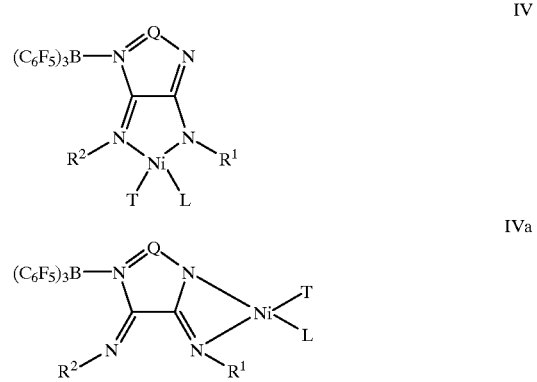

wherein R$^1$ and R$^2$ are each independently hydrocarbyl, substituted hydrocarbyl, or silyl;

Q is (i) C—R$^4$, where R$^4$ is hydrocarbyl, substituted hydrocarbyl, heteroatom connected hydrocarbyl, or heteroatom connected substituted hydrocarbyl, (ii) P(NH$_2$)$_2$, or (iii) S(NH)(NH$_2$) or S(O)(OH);

L is a monoolefin or a neutral Lewis base that can be displaced by a monoolefin; and T is hydrogen, hydrocarbyl or substituted hydrocarbyl, or may be taken together with L to form a π-allyl group.

The polymerization processes described herein may be carried out in a batch or continuous mode of operation. The processes may be conducted as solution polymerizations, as non-solvent slurry type polymerizations, as slurry polymerizations using one or more of the olefins or other solvent as the polymerization medium, or in the gas phase. The catalyst employed may be unsupported or supported using a suitable catalyst support and methods known in the art. When the catalyst is in supported form, the supported catalyst may be used in slurry or gas phase polymerizations.

Examples of "solid support" include inorganic oxide support materials such as talcs, silicas, titania, silica/chromia, silica/chromia/titania, silica/alumina, zirconia, aluminum phosphate gels, silanized silica, silica hydrogels, silica xerogels, silica aerogels, montmorillonite clay, and silica co-gels as well as organic solid supports such as polystyrene and functionalized polystyrene. See, for example, S. B. Roscoe et al., "Polyolefin Spheres from Metallocenes Supported on Non-Interacting Polystyrene," Science, 1998, 280, 270–273.

The supported catalysts may be prepared by contacting the components of the catalyst system of the present invention with the support material, e.g, silica, for a sufficient period of time to generate the supported catalysts. The metal complex and the neutral Lewis acid, if used, may be added together, as a reaction product, to the solid support. Alternatively, the metal complex component may be added to a solid support which has been pre-treated with the neutral Lewis acid component.

Polymerization temperature and pressure have significant effects on copolymer structure, composition, and molecular weight. Suitable polymerization temperatures are preferably from about −100° C. to about 200° C., more preferably in the 20° C. to 150° C. range.

After the reaction has proceeded for a time sufficient to produce the desired polymers, the polymer can be recovered from the reaction mixture by routine methods of isolation and/or purification.

High molecular weight resins are readily processed using conventional extrusion, injection molding, compression molding, and vacuum forming techniques well known in the art. Useful articles made from them include films, fibers, bottles and other containers, sheeting, molded objects and the like.

Low molecular weight resins are useful, for example, as synthetic waxes and they may be used in various wax coatings or in emulsion form. They are also particularly useful in blends with ethylene/vinyl acetate or ethylene/methyl acrylate-type copolymers in paper coating or in adhesive applications.

Although not required, typical additives used in olefin or vinyl polymers may be used in the new homopolymers and copolymers of this invention. Typical additives include pigments, colorants, titanium dioxide, carbon black, antioxidants, stabilizers, slip agents, flame retarding agents, and the like. These additives and their use in polymer systems are known per se in the art.

Other features of the invention will become apparent in the following description of working examples, which have been provided for illustration of the invention and are not intended to be limiting thereof.

EXAMPLES

The molecular weight data presented in the following examples was determined by GPC analysis in 1,2,4-trichlorobenzene at 135° C. using narrow molecular weight poly(styrene) standards for calibration and employing the appropriate Mark-Houwink-Sakurada (MHS) relations.

Example 1

Preparation of N,N'-Bis(2.6-dimethylphenyl) oxalamide 2,6-Dimethylaniline, triethylamine, and dichloromethane were dried by passage through basic alumina. A 1 L round bottom flask, equipped with a magnetic stir bar and a 125 mL pressure-equalizing dropping funnel capped by a nitrogen inlet adapter, was charged with 53.38 g of 2,6-dimethylaniline, 250 mL of dichloromethane, and 44.76 g of triethylamine. A solution of 25.34 g of oxalyl chloride in 80 mL of dichloromethane was added dropwise under nitrogen with stirring and ice-bath cooling over 1.2 hours to give a thick paste which had to be occasionally swirled by hand to effect mixing. The mixture was allowed to stir at room temperature for 14 hours, then transferred to a separatory funnel, washed 3 times with water, separated and concentrated under reduced pressure (10 mm Hg) to give 63 g of crude solid. The crude product was dissolved in a boiling mixture of 2850 mL of toluene and 1300 mL of absolute ethanol, cooled to room temperature and diluted with 260 mL of water, then allowed to crystallize for 16 hours. The resultant precipitate was isolated by vacuum filtration, washed with methanol (3×100 mL) and dried to give 39.1 g (66%) as white crystals. An additional 9.5 g (16.1%) was recovered from the filtrate by further dilution with ca. 500 mL water. Field desorption mass spectrometry showed a parent ion peak at 296 m/z. $^1$H NMR (300 MHz, $CDCl_3$, chemical shifts in ppm relative to TMS at 0 ppm): 2.29 (12 p, s), 7.15 (6 p, m), 8.86 (2 p, br s).

Example 2

Preparation of $N^1,N^2$-bis(2,6-dimethylphenyl) oxalodiimidoyl dichloride

A 1 L round bottom flask was charged with 30.0 g of N,N'-bis(2,6-dimethylphenyl)oxalamide, 58.75 g of phosphorous pentachloride and 150 mL of dry toluene, and equipped with a magnetic stir bar and a reflux condenser capped by a nitrogen inlet adapter connected to a bubbler. The mixture was heated to reflux over 30 minutes, then maintained at reflux under nitrogen for another 95 minutes to give a yellow solution. Heating was discontinued and the mixture was allowed to cool to room temperature. A short path distillation adapter and receiving flask were attached in place of the condenser, and the volatiles were removed under reduced pressure (1 mm Hg), initially at room temperature, then at 100° C., to give 20.1 g (60%) of a granular yellow solid. Field desorption mass spectrometry showed a parent ion peak at 332 m/z. $^1$H NMR (300 MHz, $C_6D_6$, chemical shifts in ppm relative to TMS at 0 ppm): 2.04 (12 p, s), 6.91 (6 p, s).

Example 3

Preparation of (2,6-dimethylphenyl)-[5-(2,6-dimethylphenylimino)-2-phenyl-5H-imidazol-4-yl] amine (compound II with Q=CPh and $R^1$=$R^2$=2, 6-dimethylphenyl)

A 100 mL, round bottom flask equipped with a magnetic stir bar and condenser capped by a nitrogen inlet adapter was charged with 347 mg of benzamidine hydrochloride hydrate, 25 mL of dry N-methylpyrrolidinone and 1.47 g of triethylamine. The mixture was stirred for 5 minutes, then treated with 499 mg of $N^1,N^2$-bis(2,6-dimethylphenyl) oxalodiimidoyl dichloride. A nitrogen atmosphere was established, then the mixture was heated to 85° C. and maintained at that temperature for 6 days. The resultant dark red-brown mixture was diluted with ether and washed with water, and the ether layer was concentrated under reduced pressure (10 mm Hg, 85° C. bath) to remove most of the volatiles. Flash chromatography ($SiO_2$, 12% EtOAc/88% hexanes) yielded 96 mg of an orange powder. Recrystallization from $CH_2Cl_2$/hexane gave 65 mg of dark violet crystals of the title compound. Field desorption mass spectrometry showed a parent ion peak at 380 m/z. $^1$H NMR (500 MHz, $CD_2Cl_2$, chemical shifts in ppm relative to TMS at 0 ppm): 2.28 (12 p, s), 7.10–7.25 (6p, s), 7.38–7.48 (2 p, m), 7.35–7.63 (1 p, m), 8.25–8.3 (2 p, m).

Example 4

Polyethylene Synthesis Using a Catalyst Generated In Situ from (2,6-dimethylphenyl)-[5-(2,6-dimethlphenylimino)-2-phenyl-5H-imidazol-4-yl] amine (compound II with Q=CPh and $R^1$=$R^2$=2, 6-dimethylphenyl) and Bis(1,5-cyclooctadiene) nickel(0)

In a drybox, a flame-dried, 200 mL, pear-shaped Schlenk flask equipped with a magnetic stir bar and capped by a septum was charged with 10 mg of (2,6-dimethylphenyl)-[5-(2,6-dimethylphenylimino)-2-phenyl-5H-imidazol4-yl] amine and 5 mg of bis(1,5-cyclooctadiene)nickel(0). On the Schlenk line, the flask was evacuated, refilled with ethylene, then charged with 45 mL of dry, deoxygenated toluene, introduced via syringe, with stirring. A transient violet color was observed, which rapidly changed to a dark green or red-green color. Ethylene uptake was observed. After 2 hours of stirring under 1 atm of ethylene at 21° C., the solution was golden-brown and methanol was added to precipitate the polymer as an oily gun. The volatiles were removed under reduced pressure (10 mm Hg initially, then 0.4 mm Hg) to give 0.20 g of a viscous beige polyethylene gum. GPC (relative to polystyrene standards) $M_n$=38,000; $M_w$=73,000. $^1$H NMR (o-dichlorobenzene-d$^4$) showed ca. 112 branches per 1000 carbons.

Example 5

Polyethylene Synthesis Using a Catalyst Generated In Situ from (2,6-dimethylphenyl)-[5-(2,6-dimethylphenylimino)-2-phenyl-5H-imidazol-4-yl]amine (compound II with Q=CPh and $R^1$=$R^2$=2, 6-dimethylphenyl, Bis(1,5-cyclooctadiene)nickel(0) and Tris(pentafluorophenyl)boron In the drybox, a flame-dried, 500 mL, round bottom flask equipped with a magnetic stir bar was charged with 8 mg of (2,6-dimethylphenyl)-[5-(2,6-dimethylphenylimino)-2-phenyl-5H-imidazol-4-yl]amine, 3 mg of bis(1,5-cyclooctadiene)nickel(0) and 120 mg of tris(pentafluorophenyl)boron, then fitted with a side-arm adapter equipped with a Kontes™ high vacuum valve and a 24/40 septum. On the Schlenk line, the flask was evacuated, refilled with ethylene, then charged with 200 mL of dry, deoxygenated toluene, introduced via syringe, with stirring. A dark red solution resulted, which subsequently became somewhat more brown and slightly purple over the next 10–20 minutes. Ethylene uptake was observed. After 60 minutes of stirring under 1 atmosphere of ethylene at 23° C., methanol and acetone were added to produce an off-white supernatant and a white flocculent precipitate of polyethylene. The polymer was isolated by vacuum filtration and dried under reduced pressure (250 mm Hg) at 100° C. for 14 h to afford 2.6 g of a white, polyethylene powder. GPC (relative to polystyrene standards) $M_n$=8,200; $M_w$=17,900. DSC: (2nd heat) melt transition with endothermic maxima at 78 and 91° C. $^1$H NMR (o-dichlorobenzene-d$^4$) showed approximately 44 branches per 1000 carbons.

Example 6

Copolymer Synthesis From Ethylene and Propene Using a Catalyst Generated In Situ from (2,6-dimethylphenyl)-[5-(2,6-dimethyphenylimino)-2-phenyl-5H-imidazol-4-yl]amine (compound II with Q=CPh and $R^1$=$R^2$=2,6-dimethylphenyl), Bis(1, 5-cyclooctadiene)nickel(0) and Tris(pentafluorophenyl)boron In the drybox, a flame-dried, 500 mL, round bottom flask equipped with a magnetic stir bar was charged with 10 mg of (2,6-dimethylphenyl)-[5-(2,6-dimethylphenylimino)-2-phenyl-5H-imidazol-4-yl]amine, 5 mg of bis(1,5-cyclooctadiene)nickel(0) and 106 mg of tris(pentafluorophenyl)boron, then fitted with an inert gas inlet adapter equipped with a Kontes™ high vacuum valve and a 24/40 septum. On the Schlenk line, the flask was evacuated, refilled with ethylene, then charged with 100 mL of dry, deoxygenated toluene, introduced via syringe, with stirring. A dark red solution resulted, which subsequently became somewhat more brown and slightly purple over the next 10 min, after which the ethylene was replaced by propene (1 atm). After a total of 120 min, the reaction was quenched with methanol and worked up to obtain the 1.8 g of the copolymer as an oily gum. GPC (relative to polystyrene standards) $M_n$=3,935; $M_w$=10,353. $^1$H NMR (500 MHz, o-dichlorobenzene-d$^4$) showed approximately 160 branches per 1000 carbons.

Example 7

Polyethylene Synthesis Using a Catalyst Generated In Situ from (2,6-dimethylphenyl)-[5-(2,6-dimethlpbenylimino)-2-phenyl-5H-imidazol4-yl]amine (compound II with Q=CPh and $R^1$=$R^2$=2, 6-dimethylphenyl). Bis(1,5-cyclooctadiene)nickel(0) and Tris(pentafluorophenyl)boron In the drybox, a flame-dried, 500 mL, round bottom flask equipped with a magnetic stir bar was charged with 10 mg of (2,6-dimethylphenyl)-[5-(2,6-dimethylphenyl)-2-phenyl-5H-imidazol-4-yl]amine, 5 mg of bis(1,5-cyclooctadiene) nickel(0) and 106 mg of tris(pentafluorophenyl)boron, then fitted with an inert gas inlet adapter equipped with a Kontes™ high vacuum valve and a 24/40 septum. On the Schlenk line, the flask was evacuated, refilled with ethylene, then charged with 100 mL of dry, deoxygenated toluene, introduced via syringe, with stirring. A dark red solution resulted, which subsequently became somewhat more brown and slightly purple over the next 10 min. After a total of 30 min stirring under an ethylene atmosphere, the reaction was quenched by the addition of methanol and acetone and the resultant precipitate was isolated by filtration and dried in vacuo to obtain 5.0 g of white, powdery polyethylene. GPC (relative to polystyrene standards) $M_n$=10,500; $M_w$=27,500. $^1$H NMR (500 MHz, o-dichlorobenzene-$^4$) showed approximately 70 branches per 1000 carbons.

Example 8

Ethylene Polymerization in the Presence of Diethyl Ether Using a Catalyst Generated In Situ from (2, 6-dimethylphenyl)-[5-(2,6-dimethylphenylimino)-2-phenyl-5H-imidazol-4-yl]amine (compound II with Q=CPh and $R^1$=$R^2$=2,6-dimethylphenyl), Bis(1, 5-cyclooctadiene)nickel(0) and Tris(pentafluorophenyl)boron In a nitrogen-filled drybox, a flame-dried, 500 mL, round bottom flask equipped with a magnetic stir bar was charged with 10.7 mg of (2,6-dimethylphenyl)-[5-(2, 6dimethylphenylimino)-2-phenyl-5H-imidazol-4-yl]amine, 3.9 mg of bis(1,5-cyclooctadiene)nickel(0) and 105 mg of tris(pentafluorophenyl)boron, then fitted with a side-arm adapter equipped with a Kontes™ high vacuum valve and a 24/40 septum. On the Schlenk line, the flask was evacuated, refilled with ethylene, then simultaneously charged via syringe with 20 mL of dry, deoxygenated diethyl ether and 80 mL dry, deoxygenated toluene, with stirring. The mixture was stirred under 1 atmosphere of ethylene for 30 min at 20° C., then methanol and acetone were added to quench the reaction. The polyethylene which separated was isolated by vacuum filtration and dried under reduced pressure at 100° C. for 14 h to afford 1.27 g of a white polyethylene powder. GPC: $M_n$=15,900 g/mol; $M_w$=56,800 g/mol. DSC: (2nd heat) melt transition with endothermic maximum 97° C. $^1$H NMR (o-dichlorobenzene-d$^4$): $M_n$=26,718 g/mol with approximately 37 branches per 1000 carbons.

Example 9

Ethylene Polymerization at Elevated Pressure (780 psig) and Temperature (40° C.) Using a Catalyst Generated In Situ from (2,6-dimethylphenyl)-[5-(2, 6-dimethylphenylimino)-2-phenyl-5H-imidazol-4-yl]amine (compound II with Q=CPh and $R^1$=$R^2$=2, 6-dimethylphenyl), Bis(1,5-cyclooctadiene)nickel(0) and Tris(pentafluorophenyl)boron A 1 L Parr™ autoclave, Model 4520 benchtop reactor, was heated and dried under vacuum, then cooled and refilled with nitrogen. Dry, deoxygenated toluene (300 mL) was added, then the autoclave was sealed and pressurized to 800 psig and vented to atmospheric pressure twice. In a nitrogen-filled drybox, septum capped vial was charged with 16.0 mg of (2,6-dimethylphenyl)-[5-(2,6-dimethylphenylimino)-2-phenyl-5H-imidazol-4-yl]amine, 6.0 mg of bis(1,5-cyclooctadiene)nickel(0) and 124 mg of tris(pentafluorophenyl)boron. At the bench, the vial was charged with 10.0 mL dry, deoxygenated toluene and shaken to afford a dark red-brown solution. Approximately 9 mL of this solution was injected into the autoclave, then the autoclave was sealed, pressurized to 780 psig, and heated to 40° C. After 25 min, 2.0 mL methanol was injected via sample loop, followed by another 2.0 mL methanol 2 min later. After a total of 90 min, the reactor was depressurized and the polymer which had formed was isolated and dried in vacuo to obtain 133 g of an off-white, powdery polyethylene. GPC: $M_n$=26,800 g/mol; $M_w$=72,200 g/mol. DSC: (2nd heat) melt transition with endothermic maximum 129° C. $^1$H NMR (o-dichlorobenzene-d$^4$): $M_n$=18,374 g/mol with approximately 8 branches per 1000 carbons.

Example 10

Ethylene Polymerization at Elevated Pressure (750 psig) in the Presence of Diethyl Ether Using a Catalyst Generated In Situ from (2,6-dimethylphenyl)-[5-(2,6-dimethylphenylimino)-2-phenyl-5H-imidazol-4-yl]amine (compound II with Q=CPh and $R^1$=$R^2$=2,6-dimethylphenyl), Bis(1,5-cyclooctadiene)nickel(0) and Tris(pentafluorophenyl)boron A 1 L Parr™ autoclave, Model 4520 benchtop reactor, was heated and dried under vacuum, then cooled and refilled with nitrogen. Dry, deoxygenated toluene (300 mL) and dry, deoxygenated diethyl ether (6.0 mL) were added, then the autoclave was sealed and pressurized to 800 psig and vented to atmospheric pressure twice. In a nitrogen-filled drybox, septum capped vial was charged with 17.0 mg of (2,6-dimethylphenyl)-[5-(2,6-dimethylphenylimino)-2-phenyl-5H-imidazol-4-yl]amine, 7.2 mg of bis(1,5-cyclooctadiene)nickel(0) and 132 mg of tris(pentafluorophenyl)boron. At the bench, the vial was charged with 10.0 mL dry, deoxygenated toluene and shaken to afford a dark red-brown solution. Approximately 6.0 mL of this solution was injected into the autoclave, then the autoclave was sealed, pressurized to 750 psig, and heated to 40° C. After 30 min, the reaction was terminated by dropping the temperature and depressurizing and opening the reactor. The polymer which had formed was dried in vacuo to obtain 40.0 g off-white polyethylene powder. GPC: $M_n$=30,600 g/mol; $M_w$=69,100 g/mol. DSC: (2nd heat) melt transition with endothermic maximum 127° C. $^1$H NMR (odichlorobenzene-d$^4$): $M_n$=23,655 g/mol with showed approximately 7 branches per 1000 carbons.

Example 11

Ethylene Polymerization in the Diethyl Ether Using a Catalyst Generated In Situ from (2,6-dimethylphenyl)-[5-(2,6-dimethylphenylimino)-2-phenyl-5H-imidazol4-yl]amine (compound II with Q=CPh and $R^1$=$R^2$=2,6-dimethylphenyl), Bis(1,5-cyclooctadiene nickel(0) and Tris(pentafluorophenyl)boron A flame-dried, 500 mL, round bottom flask equipped with a magnetic stir bar and a side-arm adapter equipped with a Kontes™ high vacuum valve and a 24/40 septum was charged with 100 mL dry, deoxygenated diethyl ether and 8 mL of a pre-mixed solution of catalyst prepared from 16.5 mg of (2,6-dimethylphenyl)-[5-(2,6-dimethylphenylimino)-2-phenyl-5H-imidazol-4-yl]amine, 5.9 mg of bis(1,5-cyclooctadiene)nickel(0), 117 mg of tris(pentafluorophenyl)boron and 8.0 mL dry, deoxygenated toluene and stirred under an ethylene atmosphere at 23° C. After 14.5 h, the volatiles were removed under reduced pressure and the residue was washed with methanol and dried in vacuo to obtain 0.9 g of a viscous polyethylene oil. GPC: $M_n$=7,640 g/mol; $M_w$32 62,500 g/mol. DSC: (2nd heat) endothermic maximum at −20° C. $^1$H NMR (o-dichlorobenzene-d$^4$): $M_n$=12988 g/mol with approximately 110 branches per 1000 carbons.

Example 12

Ethylene Polymerization at Elevated Pressure (800 psig) and temperature (50° C.) Using a Catalyst Generated In Situ from (2,6-dimethylphenyl)-[5-(2,6-dimethylphenylimino)-2-phenyl-5H-imidazol-4-yl]amine (compound II with Q=Cph and $R^1$=$R^2$=2,6-dimethylphenyl), Bis(1,5-cyclooctadiene)nickel(0) and Tris(pentafluorophenyl)boron A 1 L Parr™ autoclave, Model 4520 benchtop reactor, was heated and dried under vacuum, then cooled and refilled with nitrogen. Dry, deoxygenated toluene (300 mL) was added, then the autoclave was sealed and pressurized to 800 psig and vented to atmospheric pressure twice. In a nitrogen-filled drybox, septum capped vial was charged with 16.6 mg of (2,6-dimethylphenyl)-[5-(2,6-dimethylphenylimino)-2-phenyl-5H-imidazol-4-yl]amine, 6.1 mg of bis(1,5-cyclooctadiene)nickel(0) and 118 mg of tris(pentafluorophenyl)boron. At the bench, the vial was charged with 8.0 mL dry, deoxygenated toluene and shaken to afford a dark red-brown solution. Approximately 4 mL of this solution was injected into the autoclave, then the autoclave was sealed, pressurized to 800 psig, and heated from 25 to 50° C. over 5 min. Starting at 14 min, the reactor was depressurized, reaching ambient pressure by 18 min, whereupon the reactor was opened. The resultant polymer was recovered and dried in vacuo to obtain 31,5 g off-white polyethylene powder. GPC: $M_n$=17,600 g/mol; $M_w$=36,900 g/mol. DSC: (2nd heat) melt transition with endothermic maximum 124° C. $^1$H NMR (o-dichlorobenzene-d$^4$): $M_n$=15,245 g/mol with approximately 10 branches per 1000 carbons.

Example 13

Ethylene Polymerization at Elevated Pressure (850 psig) and temperature (65° C.) Using a Catalyst Generated In Situ from (2,6-dimethylphenyl)-[5-(2,6-dimethylphenylimino -2-phenyl-5H-imidazol-4-yl]amine (compound II with Q=Cph and $R^1$=$R^2$=2,6-dimethylpheyl), Bis(1,5-cyclooctadiene nickel(0) and Tris(pentafluorophenyl)boron A 1 L Parr™ autoclave, Model 4520 benchtop reactor, was heated and dried under vacuum, then cooled and refilled with nitrogen. Dry, deoxygenated toluene (500 mL) was added, then the autoclave was sealed and pressurized to 800 psig and vented to atmospheric pressure twice. In a nitrogen-filled drybox, septum capped vial was charged with 15.9 mg of (2,6-dimethylphenyl)-[5-(2,6-dimethylphenylimino)-2-phenyl-5H-imidazol-4yl]amine, 6.5 mg of bis(1,5-cyclooctadiene)nickel(0) and 131 mg of tris (pentafluorophenyl)boron. At the bench, the vial was charged with 8.0 mL dry, deoxygenated toluene and shaken to afford a dark red-brown solution. Approximately 4 mL of this solution was injected into the autoclave, then the autoclave was sealed, pressurized to 800 psig, and heated from 25 to 65° C. over 6 min. Starting at 28.5 min, the reactor was depressurized, reaching ambient pressure by 31 min, whereupon the reactor was opened. The resultant polymer was recovered and dried in vacuo to obtain 12.5 g white, somewhat resilient, polyethylene powder. GPC: $M_n$=12,000 g/mol; $M_w$=27,300 g/mol. DSC: (2nd heat) melt transition with endothermic maxima at 117, 105° C. $^1$H NMR (o-dichlorobenzene-$d^4$): $M_n$=12,444 g/mol with approximately 21 branches per 1000 carbons.

Example 14

Preparation of a Silica-Supported Catalyst from (2, 6-dimethylphenyl)-[5-(2,6-dimethylphenylimino-2-phenyl-5H-imidazol-4-yl]amine (compound II with Q=Cph and $R^1$=$R^2$=2,6-dimethylphenyl), Bis(1,5-cyclooctadiene)nickel(0) and Tris (pentafluorophenyl)boron In a nitrogen-filled drybox, 24.4 mg of (2,6-dimethylphenyl)-[5-(2,6-dimethylphenylimino)-2-phenyl-5H-imidazol-4-yl]amine, 15.1 mg of bis(1,5-cyclooctadiene)nickel(0) and 39.2 mg of tris (pentafluorophenyl)boron were reacted in 4 mL dry toluene for 7 min, and the resultant solution was added to a suspension of 2.00 g silica (Grace Davison Sylopol 2402, lot 98–52) in 12 mL toluene, using 4 mL toluene to complete the transfer. The mixture was stirred for 10 min, then transferred to a Schlenk line and concentrated to dryness under vacuum over 90 min. This afforded 2.4 g of the supported catalyst as a free-flowing powder, still containing a small amount of toluene.

Example 15

Gas Phase Ethylene Polymerization at Elevated Pressure (925 psig) and Temperature (50° C.) Using a Silica-Supported Catalyst Derived from (2,6-dimethyphenyl)-[5-(2,6-dimethylphenylimino)-2-phenyl-5H-imidazol-4-yl]amine (compound II with Q=CPh and $R^1$=$R^2$=2,6-dimethylphenyl), Bis(1,5-cyclooctadiene)nickel(0) and Tris (pentafluorophenyl)boron A 1 L Parr™ autoclave, Model 4520 benchtop reactor, was heated and dried under vacuum, then cooled and refilled with nitrogen and charged in 500 g dry sodium chloride and 493 mg of the supported catalyst prepared as described above in Example 14. The reactor was sealed and pressurized to 925 psig with ethylene and heated from 25 to 50° C. over 34 min, after which the temperature was maintained at 49–51° C. After a total of 91 min, the reactor was depressurized and opened. The resultant mixture of polymer and salt was washed with water (in a blender) and the polymer which separated was filtered and dried to obtain 32.9 g of a very powdery, off-white polyethylene. GPC: $M_n$=12,500 g/mol; $M_w$=181,100 g/mol. DSC: (2nd heat) melt transition with endothermic maximum at 132° C. $^1$H NMR (o-dichlorobenzene-$d^4$): $M_n$=14,157 g/mol with approximately 5 branches per 1000 carbons.

While the invention has been described with reference to preferred embodiments and working examples, it is to be understood that variations and modifications may be resorted to as will be apparent to those skilled in the art. Such variations and modifications are to be considered within the purview and scope of the invention as defined by the claims appended hereto.

We claim:

1. A process for the production of polyolefins, comprising: contacting, at a temperature from about −100° C. to about 200° C., one or more monomers of the formula RCH=CHR$^3$ with a catalyst comprising (i) a transition metal complex of formula I or Ia, and, optionally, (ii) a neutral Lewis acid;

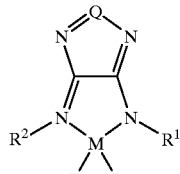

I

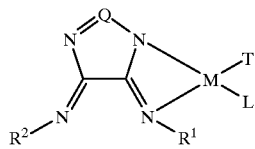

Ia wherein R and $R^3$ are each, independently, hydrogen, hydrocarbyl or substituted hydrocarbyl and may be linked to form a cyclic olefin;

$R^1$ and $R^2$ are each independently hydrocarbyl, substituted hydrocarbyl, or silyl;

Q is (i) C—$R^4$, where $R^4$ is hydrocarbyl, substituted hydrocarbyl, heteroatom connected hydrocarbyl, or heteroatom connected substituted hydrocarbyl, (ii) P(NH$_2$)$_2$, or (iii) S(NH)(NH$_2$) or S(O)(OH);

L is a monoolefin or a neutral Lewis base that can be displaced by a monoolefin;

T is hydrogen, hydrocarbyl or substituted hydrocarbyl, or may be taken together with L to form a π-allyl group; and M is Ni(II), Pd(II), Co(II) or Fe(II).

2. The process of claim 1, wherein M is Ni(II).

3. The process of claim 2, wherein Q is C—$R^4$, where $R^4$ is hydrocarbyl, substituted hydrocarbyl, heteroatom connected hydrocarbyl, or heteroatom connected substituted hydrocarbyl.

4. The process of claim 3, wherein the monomer is ethylene, propylene, 1-butene, 1-pentene, 1-hexene, or 1-octene.

5. The process of claim 1, wherein a neutral Lewis acid is used.

6. The process of claim 5, wherein M is Ni(II).

7. The process of claim 6, wherein Q is C—$R^4$, where $R^4$ is hydrocarbyl, substituted hydrocarbyl, heteroatom connected hydrocarbyl, or heteroatom connected substituted hydrocarbyl.

8. The process of claim 7, wherein the monomer is ethylene, propylene, 1-butene, 1-pentene, 1-hexene, or 1-octene.

9. A process for the production of polyolefins, comprising: contacting, at a temperature from about −100° C. to about 200° C., one or more monomers of the formula RCH=CHR$^3$ with a supported catalyst comprising (i) a transition metal complex of formula I or Ia, and, optionally, (ii) a neutral Lewis acid;

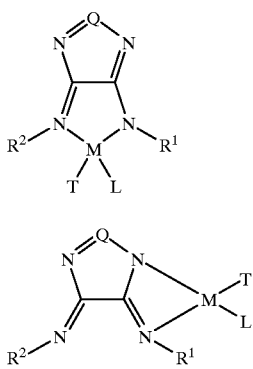

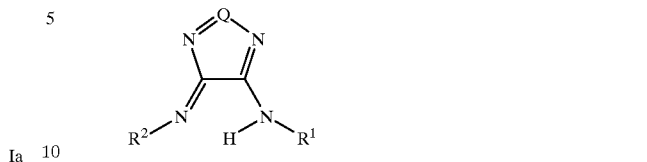

wherein R and R³ are each, independently, hydrogen, hydrocarbyl or substituted hydrocarbyl and may be linked to form a cyclic olefin;

R¹ and R² are each independently hydrocarbyl, substituted hydrocarbyl, or silyl;

Q is (i) C—R⁴, where R⁴ is hydrocarbyl, substituted hydrocarbyl, heteroatom connected hydrocarbyl, or heteroatom connected substituted hydrocarbyl, (ii) P(NH₂)₂, or (iii) S(NH)(NH₂) or S(O)(OH);

L is a monoolefin or a neutral Lewis base that can be displaced by a monoolefin;

T is hydrogen, hydrocarbyl or substituted hydrocarbyl, or may be taken together with L to form a π-allyl group; and M is Ni(II), Pd(II), Co(II) or Fe(II).

10. The process of claim 9, wherein M is Ni(II).

11. The process of claim 10, wherein Q is C—R⁴, where R⁴ is hydrocarbyl, substituted hydrocarbyl, heteroatom connected hydrocarbyl, or heteroatom connected substituted hydrocarbyl.

12. The process of claim 11, wherein the monomer is ethylene, propylene, 1-butene, 1-pentene, 1-hexene, or 1-octene.

13. The process of claim 9, wherein a neutral Lewis acid is used.

14. The process of claim 13, wherein M is Ni(II).

15. The process of claim 14, wherein Q is C—R⁴, where R⁴ is hydrocarbyl, substituted hydrocarbyl, heteroatom connected hydrocarbyl, or heteroatom connected substituted hydrocarbyl.

16. The process of claim 15, wherein the monomer is ethylene, propylene, 1-butene, 1-pentene, 1-hexene, or 1-octene.

17. The process of claim 9, wherein the supported catalyst comprises a silica support material.

18. The process of claim 17, wherein a neutral Lewis acid is used.

19. The process of claim 18, wherein the neutral Lewis acid is B(C₆F₅)₃, methylaluminoxane, BPh₃, or B(3,5-(CF₃)C₆H₃)₃.

20. The process of claim 9, wherein the supported catalyst comprises silica and methylaluminoxane.

21. A process for the polymerization of olefins, comprising:

contacting, at a temperature from about −100° C. to about 200° C., one or more monomers of the formula RCH═CHR³ with a catalyst comprising the reaction product of (i) a compound of the formula II, or tautomers thereof, (ii) a suitable precursor selected from the group consisting of Ni, Pd, Co, and Fe compounds, and, optionally, (iii) a neutral Lewis acid;

II

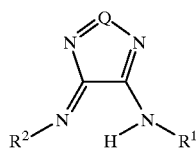

wherein R and R³ are each, independently, hydrogen, hydrocarbyl or fluoroalkyl and may be linked to form a cyclic olefin;

R¹ and R² are each independently hydrocarbyl, substituted hydrocarbyl, or silyl; and Q is (i) C—R⁴, wherein R⁴ is hydrocarbyl, substituted hydrocarbyl, heteroatom connected hydrocarbyl, or heteroatom connected substituted hydrocarbyl, (ii) P(NH₂)₂, or (iii) S(NH)(NH₂) or S(O)(OH).

22. The process of claim 21, wherein the suitable precursor is a zerovalent Ni compound.

23. The process of claim 22, wherein Q is C—R⁴, where R⁴ is hydrocarbyl, substituted hydrocarbyl, heteroatom connected hydrocarbyl, or heteroatom connected substituted hydrocarbyl.

24. The process of claim 23, wherein the monomer is ethylene, propylene, 1-butene, 1-pentene, 1-hexene, 1-octene, or cyclopentene.

25. The process of claim 21, wherein a neutral Lewis acid is used.

26. The process of claim 25, wherein the suitable precursor is a zerovalent Ni compound.

27. The process of claim 26, wherein Q is C—R⁴, where R⁴ is hydrocarbyl, substituted hydrocarbyl, heteroatom connected hydrocarbyl, or heteroatom connected substituted hydrocarbyl.

28. The process of claim 27, wherein the monomer is ethylene, propylene, 1-butene, 1-pentene, 1-hexene, 1-octene, or cyclopentene.

29. A process for the polymerization of olefins, comprising:

contacting, at a temperature from about −100° C. to about 200° C., one or more monomers of the formula RCH═CHR³ with a supported catalyst comprising the reaction product of (i) a compound of the formula II, or tautomers thereof, (ii) a suitable precursor selected from the group consisting of Ni, Pd, Co, and Fe compounds, and, optionally, (iii) a neutral Lewis acid;

II wherein R and R³ are each, independently, hydrogen, hydrocarbyl or fluoroalkyl and may be linked to form a cyclic olefin;

R¹ and R² are each independendly hydrocarbyl, substituted hydrocarbyl, or silyl; and Q is (i) C—R⁴, wherein R⁴ is hydrocarbyl, substituted hydrocarbyl, heteroatom connected hydrocarbyl, or heteroatom connected substituted hydrocarbyl, (ii) P(NH₂)₂, or (iii) S(NH)(NH₂) or S(O)(OH).

30. The process of claim 29, wherein the suitable precursor is a zerovalent Ni compound.

31. The process of claim 30, wherein Q is C—$R^4$, where $R^4$ is hydrocarbyl, substituted hydrocarbyl, heteroatom connected hydrocarbyl, or heteroatom connected substituted hydrocarbyl.

32. The process of claim 31, wherein the monomer is ethylene, propylene, 1-butene, 1-pentene, 1-hexene, 1-octene, or cyclopentene.

33. The process of claim 29, wherein a neutral Lewis acid is used.

34. The process of claim 33, wherein the suitable precursor is a zerovalent Ni compound.

35. The process of claims 34, wherein Q is C—$R^4$, where $R^4$ is hydrocarbyl, substituted hydrocarbyl, heteroatom connected hydrocarbyl, or heteroatom connected substituted hydrocarbyl.

36. The process of claim 35, wherein the monomer is ethylene, propylene, 1-butene, 1-pentene, 1-hexene, 1octene, or cyclopentene.

37. The process of claim 29, wherein the supported catalyst comprises a silica support material.

38. The process of claim 37, wherein a neutral Lewis acid is used.

39. The process of claim 38, wherein the neutral Lewis acid is $B(C_6F_5)_3$, methylaluminoxane, $BPh_3$, or $B(3,5-(CF_3)C_6H_3)_3$.

40. The process of claim 29, wherein the supported catalyst comprises silica and methylaluminoxane.

41. A process for the polymerization of olefins, comprising: contacting one or more monomers of the formula RCH=$CHR^3$ with a catalyst comprising the reaction product of (i) a binucleating or multinucleating ligand complexed to a Group 8–10 transition metal M and (ii) one or more neutral Lewis acids, wherein the Lewis acid or acids are bound to one or more heteroatoms which are π-conjugated to the donor atom or atoms bound to the transition metal M;

R and $R^3$ each, independently, represent a hydrogen, a hydrocarbyl, a fluoroalkyl, or may be linked to form a cyclic olefin;

M is Ni(II); and the binucleating or multinucleating ligand is a compound of formula II, or tautomers thereof:

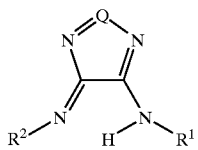

II wherein $R^1$ and $R^2$ are both sterically hindered aryl rings; and

Q is (i) C—$R^4$, where $R^4$ is hydrocarbyl, substituted hydrocarbyl, heteroatom connected hydrocarbyl, or heteroatom connected substituted hydrocarbyl, (ii) $P(NH_2)_2$, or (iii) $S(NH)(NH_2)$ or $S(O)(OH)$.

42. The process of claim 41, wherein Q is C—$R^4$, where $R^4$ is hydrocarbyl, substituted hydrocarbyl, heteroatom connected hydrocarbyl, or heteroatom connected substituted hydrocarbyl.

43. The process of claim 42, wherein the Lewis acid is a boron or aluminum containing neutral Lewis acid.

44. A process for the polymerization of olefins, comprising: contacting one or more monomers of the formula RCH=$CHR^3$ with a supported catalyst comprising the reaction product of (i) a binucleating or multinucleating ligand complexed to a Group 8–10 transition metal M and (ii) one or more neutral Lewis acids, wherein the Lewis acid or acids are bound to one or more heteroatoms which are π-conjugated to the donor atom or atoms bound to the transition metal M; wherein R and $R^3$ each, independently, represent a hydrogen, a hydrocarbyl, a fluoroalkyl, or may be linked to form a cyclic olefin; wherein M is Ni(II); and wherein the binucleating or multinucleating ligand is a compound of formula II, or tautomers thereof:

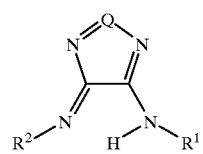

II wherein $R^1$ and $R^2$ are both sterically hindered aryl rings; and

Q is (i) C—$R^4$, where $R^4$ is hydrocarbyl, substituted hydrocarbyl, heteroatom connected hydrocarbyl, or heteroatom connected substituted hydrocarbyl, (ii) $P(NH_2)_2$, or (iii) $S(NH)(NH_2)$ or $S(O)(OH)$.

45. The process of claim 44, wherein Q is C—$R^4$, where $R^4$ is hydrocarbyl, substituted hydrocarbyl, heteroatom connected hydrocarbyl, or heteroatom connected substituted hydrocarbyl.

46. The process of claim 45, wherein the Lewis acid is a boron or aluminum containing neutral Lewis acid.

47. A process for the polymerization of olefins, comprising:

contacting, at a temperature from about −100° C. to about 200° C., one or more monomers of the formula RCH=$CHR^3$, with a catalyst comprising the reaction product of (i) an anionic compound of the formula II, (ii) a suitable divalent metal precursor selected from the group consisting of Ni(II), Pd(II), Co(II), and Fe(II) compounds, and, optionally, (iii) a neutral Lewis acid;

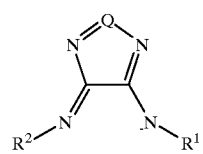

III wherein R and $R^3$ are each, independently, hydrogen, hydrocarbyl or fluoroalkyl and may be linked to form a cyclic olefin;

$R^1$ and $R^2$ are each independently hydrocarbyl, substituted hydrocarbyl, or silyl; and Q is C—$R^4$, where $R^4$ is hydrocarbyl, substituted hydrocarbyl, heteroatom connected hydrocarbyl, heteroatom connected substituted hydrocarbyl, or O-Si(tert-butyl)$(CH_3)_2$.

48. The process of claim 47, wherein the suitable divalent metal precursor is a Ni(II) compound.

49. The process of claim 48, wherein Q is C—$R^4$, where $R^4$ is hydrocarbyl or substituted hydrocarbyl.

50. The process of claim 49, wherein the monomer is ethylene, propylene, 1-butene, 1-pentene, 1-hexene, 1-octene, or cyclopentene.

51. The process of claim 47, wherein a neutral Lewis acid is used.

52. The process of claim 51, wherein the suitable divalent metal precursor is a Ni(II) compound.

53. The process of claim 52, wherein Q is C—$R^4$, where $R^4$ is phenyl, pentafluorophenyl, trifluoromethyl, fluoroalkyl, O—Si(tert-butyl)($CH_3$)$_2$, $SCH_3$, 4-methoxyphenyl, 4-cyanophenyl, trifluoromethyl, or 4-nitrophenyl.

54. The process of claim 53, wherein the monomer is ethylene, propylene, 1-butene, 1-pentene, 1-hexene, 1-octene, or cyclopentene.

55. A process for the polymerization of olefins, comprising:

contacting, at a temperature from about −100° C. to about 200° C., one or more monomers of the formula RCH=CHR$^3$, with a supported catalyst comprising the reaction product of (i) an anionic compound of the formula III, (ii) a suitable divalent metal precursor selected from the group consisting of Ni(II), Pd(II), Co(II), and Fe(II) compounds, and, optionally, (iii) a neutral Lewis acid;

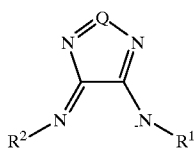

III wherein R and $R^3$ are each, independently, hydrogen, hydrocarbyl or fluoroalkyl and may be linked to form a cyclic olefin;

$R^1$ and $R^2$ are each independently hydrocarbyl, substituted hydrocarbyl, or silyl; and Q is C—$R^4$, where $R^4$ is hydrocarbyl, substituted hydrocarbyl, heteroatom connected hydrocarbyl, heteroatom connected substituted hydrocarbyl, or O-Si(tert-butyl)($CH_3$)$_2$.

56. The process of claim 55, wherein the suitable divalent metal precursor is a Ni(II) compound.

57. The process of claim 56, wherein Q is C—$R^4$, where $R^4$ is hydrocarbyl or substituted hydrocarbyl.

58. The process of claim 57, wherein the monomer is ethylene, propylene, 1-butene, 1-pentene, 1-hexene, 1-octene, or cyclopentene.

59. The process of claim 55, wherein a neutral Lewis acid is used.

60. The process of claim 59, wherein the suitable divalent metal precursor is a Ni(II) compound.

61. The process of claim 60, wherein Q is C—$R^4$, where $R^4$ is phenyl, pentafluorophenyl, trifluoromethyl, fluoroalkyl, O—Si(tert-butyl)($CH_3$)$_2$, $SCH_3$, 4-methoxyphenyl, 4-cyanophenyl, trifluoromethyl, or 4-nitrophenyl.

62. The process of claim 61, wherein the monomer is ethylene, propylene, 1-butene, 1-pentene, 1-hexene, 1-octene, or cyclopentene.

63. The process of claim 55, wherein the supported catalyst comprises a silica support material.

64. The process of claim 63, wherein a neutral Lewis acid is used.

65. The process of claim 64, wherein the neutral Lewis acid is B($C_6F_5$)$_3$, methylaluminoxane, BPh$_3$, or B(3,5-($CF_3$)$C_6H_3$)$_3$.

66. The process of claim 55, wherein the supported catalyst comprises silica and methylaluminoxane.

67. A process for the production of polyolefins, comprising:

contacting, at a temperature from about −100° C. to about 200° C., one or more monomers of the formula RCH=CHR$^3$ with a catalyst comprising (i) a transition metal complex of formula V or Va, or tautomers thereof, and, optionally, (ii) a neutral Lewis acid;

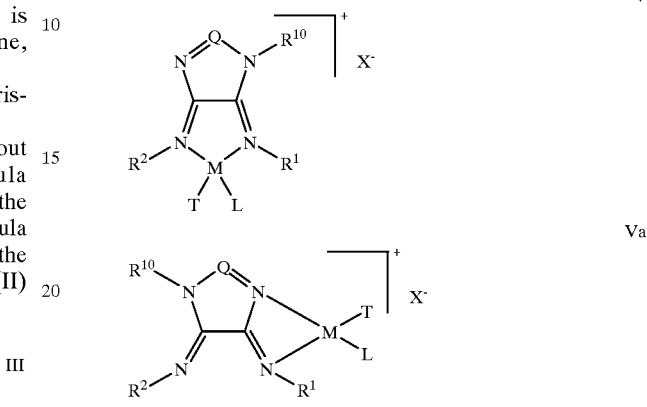

wherein R and $R^3$ are each, independently, hydrogen, hydrocarbyl or substituted hydrocarbyl and may be linked to form a cyclic olefin;

$R^1$ and $R^2$ are each independently hydrocarbyl, substituted hydrocarbyl, or silyl;

Q is (i) C—$R^4$, where $R^4$ is hydrocarbyl, substituted hydrocarbyl, heteroatom connected hydrocarbyl, or heteroatom connected substituted hydrocarbyl, (ii) P(NH$_2$)$_2$, or (iii) S(NH)(NH$_2$) or S(O)(OH);

L is a monoolefin or a neutral Lewis base that can be displaced by a monoolefin;

T is hydrogen, hydrocarbyl or substituted hydrocarbyl, or may be taken together with L to form a π-allyl group;

M is Ni(II), Pd(II), Co(II) or Fe(II);

$R^{10}$ is hydrogen, hydrocarbyl, substituted hydrocarbyl, or silyl; and

X is a weakly coordinating anion.

68. The process of claim 67, wherein M is Ni(II).

69. The process of claim 68, wherein Q is C—$R^4$, where $R^4$ is hydrocarbyl, substituted hydrocarbyl, heteroatom connected hydrocarbyl, or heteroatom connected substituted hydrocarbyl.

70. The process of claim 69, wherein the monomer is ethylene, propylene, 1-butene, 1-pentene, 1-hexene, or 1-octene.

71. The process of claim 67, wherein a neutral Lewis acid is used.

72. The process of claim 71, wherein M is Ni(II).

73. The process of claim 72, wherein Q is C—$R^4$, where $R^4$ is hydrocarbyl, substituted hydrocarbyl, heteroatom connected hydrocarbyl, or heteroatom connected substituted hydrocarbyl.

74. The process of claim 73, wherein the monomer is ethylene, propylene, 1-butene, 1-pentene, 1-hexene, or 1-octene.

75. The process of claim 67, wherein the catalyst is attached to a solid support.

76. The process of claim 75, wherein the solid support is silica.

77. A process for the production of polyolefins, comprising:

contacting, at a temperature from about −100° C. to about 200° C., one or more monomers of the formula RCH=CHR³ with a catalyst comprising (i) a transition metal complex of formula VI or VIa, and (ii) a neutral Lewis acid;

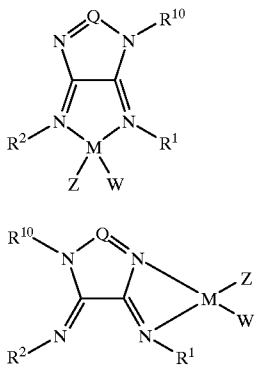

VI

VIa wherein R and R³ are each, independently, hydrogen, hydrocarbyl or substituted hydrocarbyl and may be linked to form a cyclic olefin;

R¹ and R² are each independently hydrocarbyl, substituted hydrocarbyl, or silyl;

Q is (i) C—R⁴, where R⁴ is hydrocarbyl, substituted hydrocarbyl, heteroatom connected hydrocarbyl, or heteroatom connected substituted hydrocarbyl, (ii) P(NH₂)₂, or (iii) S(NH)(NH₂) or S(O)(OH);

Z and W each independently represent Cl, Br, I, methyl, or H;

M is Ni(II), Pd(II), Co(II) or Fe(II); and

R¹⁰ is hydrogen, hydrocarbyl, substituted hydrocarbyl, or silyl.

78. The process of claim 77, wherein M is Ni(II).

79. The process of claim 78, wherein Q is C—R⁴, where R⁴ is hydrocarbyl, substituted hydrocarbyl, heteroatom connected hydrocarbyl, or heteroatom connected substituted hydrocarbyl.

80. The process of claim 79, wherein the monomer is ethylene, propylene, 1-butene, 1-pentene, 1-hexene, or 1-octene.

81. The process of claim 77, wherein a neutral Lewis acid is used.

82. The process of claim 81, wherein M is Ni(II).

83. The process of claim 82, wherein Q is C—R⁴, where R⁴ is hydrocarbyl, substituted hydrocarbyl, heteroatom connected hydrocarbyl, or heteroatom connected substituted hydrocarbyl.

84. The process of claim 83, wherein the monomer is ethylene, propylene, 1-butene, 1-pentene, 1-hexene, or 1-octene.

85. The process of claim 77, wherein the catalyst is attached to a solid support.

86. The process of claim 85, wherein the solid support is silica.

* * * * *